US008603439B2

(12) United States Patent
Montgomery

(10) Patent No.: US 8,603,439 B2
(45) Date of Patent: Dec. 10, 2013

(54) FORMULATIONS OF AMINOGLYCOSIDE AND FOSFOMYCIN COMBINATIONS AND METHODS AND SYSTEMS FOR TREATMENT OF VENTILATOR ASSOCIATED PNEUMONIA (VAP) AND VENTILATOR ASSOCIATED TRACHEAL (VAT) BRONCHITIS

(75) Inventor: Alan Bruce Montgomery, Seattle, WA (US)

(73) Assignee: Cardeas Pharma Inc., Seattle, WA (US)

( * ) Notice: Subject to any disclaimer, the term of this patent is extended or adjusted under 35 U.S.C. 154(b) by 0 days.

(21) Appl. No.: 13/548,115

(22) Filed: Jul. 12, 2012

(65) Prior Publication Data

US 2013/0014759 A1 Jan. 17, 2013

Related U.S. Application Data

(60) Provisional application No. 61/572,225, filed on Jul. 12, 2011.

(51) Int. Cl.
*A61K 9/14* (2006.01)
*A61K 9/12* (2006.01)

(52) U.S. Cl.
USPC ............................................. 424/46; 424/45

(58) Field of Classification Search
None
See application file for complete search history.

(56) References Cited

U.S. PATENT DOCUMENTS

| 5,508,269 | A | 4/1996 | Smith et al. |
|---|---|---|---|
| 6,387,886 | B1 | 5/2002 | Montgomery et al. |
| 6,615,824 | B2 | 9/2003 | Power |
| 6,968,840 | B2 | 11/2005 | Smith et al. |
| 7,100,600 | B2 | 9/2006 | Loeffler et al. |
| 7,607,436 | B2 | 10/2009 | Smaldone et al. |
| 7,943,118 | B2 | 5/2011 | Baker et al. |
| 7,971,588 | B2 | 7/2011 | Fink et al. |
| 8,196,573 | B2 | 6/2012 | Fink et al. |
| 8,336,545 | B2 | 12/2012 | Fink et al. |
| 2006/0073156 | A1 | 4/2006 | Ungheri et al. |
| 2007/0116649 | A1 | 5/2007 | Charan et al. |
| 2007/0218013 | A1 | 9/2007 | Baker et al. |
| 2009/0032427 | A1 | 2/2009 | Cheu et al. |
| 2010/0063005 | A1 | 3/2010 | Fiala |
| 2010/0282247 | A1 | 11/2010 | Kadrichu et al. |
| 2010/0286031 | A1 | 11/2010 | Charan et al. |
| 2011/0117030 | A1 | 5/2011 | Baker et al. |
| 2011/0124589 | A1 | 5/2011 | Bhatt et al. |
| 2011/0189103 | A1 | 8/2011 | Baker et al. |
| 2011/0257078 | A1 | 10/2011 | Young et al. |
| 2012/0058198 | A1 | 3/2012 | Clarke et al. |
| 2012/0101055 | A1 | 4/2012 | Speirs et al. |
| 2012/0148641 | A1 | 6/2012 | Challoner et al. |
| 2012/0225835 | A1 | 9/2012 | Charan et al. |
| 2012/0247462 | A1 | 10/2012 | Charan et al. |

FOREIGN PATENT DOCUMENTS

WO WO 2005/110022 A2 11/2005

OTHER PUBLICATIONS

WO, International Search Report for PCT/US2012/046559, Date of Issuance Sep. 17, 2012.
Jones, Andrew M., et al., "Emerging Treatments in Cystic Fibrosis", *Drugs*, vol. 69, No. 14, pp. 1903-1910, Jan. 1, 2009.
Tessier, F., et al., "In vitro activity of fosfomycin combined with ceftazidime, imipenem, amikacin and ciprofloxacin again *Pseudomonas aeruginosa*", *European Journal of Clinical Microbiology & Infectious Diseases*, Springer, Weisbaden, DE, vol. 16, pp. 159-162, Jan. 1, 1997.
Alvarez, S. et al., "In vitro activity of fosfomycin, alone and in combination, against methicillin-resistant *Staphylococcus aureus*", Antimicrob Agents Chemother, pp. 689-690 (Nov. 1985).
American Thoracic Society Documents, "Guidelines for the Management of Adults with Hospital-acquired, Ventilator-associated and Healthhcare-associated Pneumonia", Am J Respir Crit Care Med, vol. 171, pp. 388-416, DOI: 10.1164/rccm.200405-644ST (2005).
Cai, Y. et al., "Synergistic effects of aminoglycosides and fosfomycin on *Pseudomonas aeruginosa* in vitro and biofilm infections in a rat model", J Antimicrob Chemother, pp. 563-566 (Sep. 2009).
Eschenbacher, W.L. et al., "Alteration in osmolarity of inhaled aerosols cause bronchoconstriction and cough, but absence of a permeant anion causes cough alone", Am Rev Respir Dis, pp. 211-215 (Feb. 1984).
Hahn, M. et al., "In Vitro Assessment of a Novel Nebulizer for Mechanically Ventilated Patients Based on the eFlow Technology", International Society for Aerosols in Medicine, ISAM 2009, 17th Congress, May 10-14, 2009.
Joseph, N.M. et al., "Ventilator-associated pneumonia: a review", Eur J Intern Med, pp. 360-368 (Oct. 2010).
Koenig, S.M., et al., "Ventilator-Associated Pneumonia: Diagnosis, Treatment, and Prevention" Clinical Microbiology Reviews, American Society for Microbiology, doi:10.1128/CMR.00051-05 pp. 637-657 (Oct. 2006).
Lu, Q. et al., "Nebulized ceftazidime and amikacin in ventilator-associated pneumonia caused by *Pseudomonas aeruginosa*", Am J Respir Crit Care Med, pp. 106-115 (Jul. 2011).
MacLeod, D.L. et al., "Antibacterial activities of a fosfomycin/ tobramycin combination: a novel inhaled antibiotic for bronchiectasis", J Antimicrob Chemother, pp. 829-836, (Oct. 2009).
Mendelman, P.M. et al., "Aminoglycoside penetration, inactivation, and efficacy in cystic fibrosis sputum", Am Rev Respir Dis, pp. 761-765 (Oct. 1985).
Miller, D.D. et al., "Aerosol Delivery and Modern Mechanical Ventilation, In Vitro/In Vivo Evaluation", Am J Respir Crit Care Med, pp. 1205-1209 (Jul. 2003).

(Continued)

*Primary Examiner* — Robert A Wax
*Assistant Examiner* — Randeep Singh
(74) *Attorney, Agent, or Firm* — Orrick, Herrington & Sutcliffe LLP

(57) ABSTRACT

The present invention is antibiotic compositions, ventilator based systems and methods relating to ventilator-associated pneumonia (VAP) and ventilator-associated tracheal (VAT) bronchitis. Antibiotic combinations of fosfomycin and an aminoglycoside, preferably amikacin, are administered via an in-line nebulizer within the airway of the ventilator. Humidified conditions create an improved aerosol mist to treat VAP and VAT.

35 Claims, 1 Drawing Sheet

(56) References Cited

OTHER PUBLICATIONS

Niederman, M.S. et al., "BAY41-6551 achieves bactericidal tracheal aspirate amikacin concentrations in mechanically ventilated patients with Gram-negative pneumonia", Intensive Care Medicine, vol. 38, Issue 2, pp. 263-271 (Feb. 2012).

Niederman, M. et al., "NKTR-061 (Inhaled Amikacin) Reduces Intravenous Antibioitc Use of Incubated Mechanically Ventilated Patients During Treatment of Gram-Negative Pneumonia", [Critical Care] 27th International Symposium on Intensive Care and Emergency Medicine, S38 P97-eoa (Mar. 2007).

Nseir, S. et al., "Nosocomial tracheobronchitis", Current Opinion in Infectious Diseases, pp. 148-153 (2009).

Palmer, L.B. et al., "Aerosolized antibiotics in mechanically ventilated patients: Delivery and response", Critical Care Med, vol. 26, No. 1, pp. 31-39 (Jan. 1998).

Palmer, L.B. et al., "Aerosolized antibiotics and ventilator-associated tracheobronchitis in the intensive care unit", Critical Care Med, vol. 36, No. 7, pp. 2008-2013 (Jul. 2008).

Sogaard, O.S. et al., "A binational cohort study of ventilator-assisted pneumonia in Denmark and Australia", Scand J Infec Dis, pp. 256-264 (2006).

Takahashi, K. et al., "Synergistic Activities of Combinations of β-Lactams, Fosfomycin, and Tobramycin Against *Pseudomonas aeruginosa*", Antimicrobial Agents and Chemotherapy, pp. 789-791 (Nov. 1984).

Trapnell, B.C. et al., "Fosfomycin/Tobramycin for Inhalation in Patients with Cystic Fibrosis with *Pseudomonas* Airway Infection", Am J Respir Crit Care Med, vol. 185, Iss. 2, pp. 171-178 (Jan. 2012).

Trapnell, B.C. et al., "Poster 233: Fosfomycin/Tobramycin for Inhalation (FTI): Efficacy Results of a Phase 2 Placebo controlled Trial in Patients with Cystic Fibrosis and *Pseudomonas aeruginosa*", [Pediatric pulmonology] 24th Annual North American Cystic Fibrosis Conference, pp.[45]([suppl 33]), (Oct. 2010).

Trapnell, B.C. et al., "Poster 234: Fosfomycin/Tobramycin for Inhalation (FTI): Safety Results of a Phase 2 Placebo controlled Trial in Patients with Cystic Fibrosis and *Pseudomonas aeruginosa*", [Pediatric pulmonology] 24th Annual North American Cystic Fibrosis Conference, pp.[45]([suppl 33]), (Oct. 2010).

Wood, G.C. et al., "Aerosolized Ceftazidime for Prevention of Ventilator-Associated Pneumonia and Drug Effects on the Proinflammatory Response in Critically Ill Trauma Patients", Pharmacotherapy, vol. 22, pp. 972-982 (Nov. 2002).

Zhanel, G.G. et al., "Antimicrobial susceptibility of 15,644 pathogens from Canadian hospitals: results of the CANWARD 2007-2009 study", Diagn Microbiol Infect Dis, pp. 291-306 (Mar. 2011).

"28th International Symposium on Intensive Care and Emergency Medicine", Mar. 18-21, 2008, Critical Care, vol. 12, Suppl 2, pp. S1-S212 (2008).

Miller, Dorisanne D. et al., Aerosol Delivery and Modern Mechanical Ventilation, American Journal of Respiratory and Critical Care Medicine, vol. 168, 2003,, 5 pages.

Goldstein, Iva, et al., Lung Deposition and Efficiency of Nebulized Amikacin during *Escherichia coli* Pneumonia in Ventilated Piglets, American Journal of Respiratory and Critical Care Medicine, vol. 166, 2002, 7 pages.

Ferrari, Fabio et al., Lack of Lung Tissue and Systemic Accumulation after Consecutive Daily Aerosols of Amikacin in Bentilated Piglets with Healthy Lungs, Anesthesiology, V 98, No. 4, Apr. 2003, p. 1016-1019 4 pages.

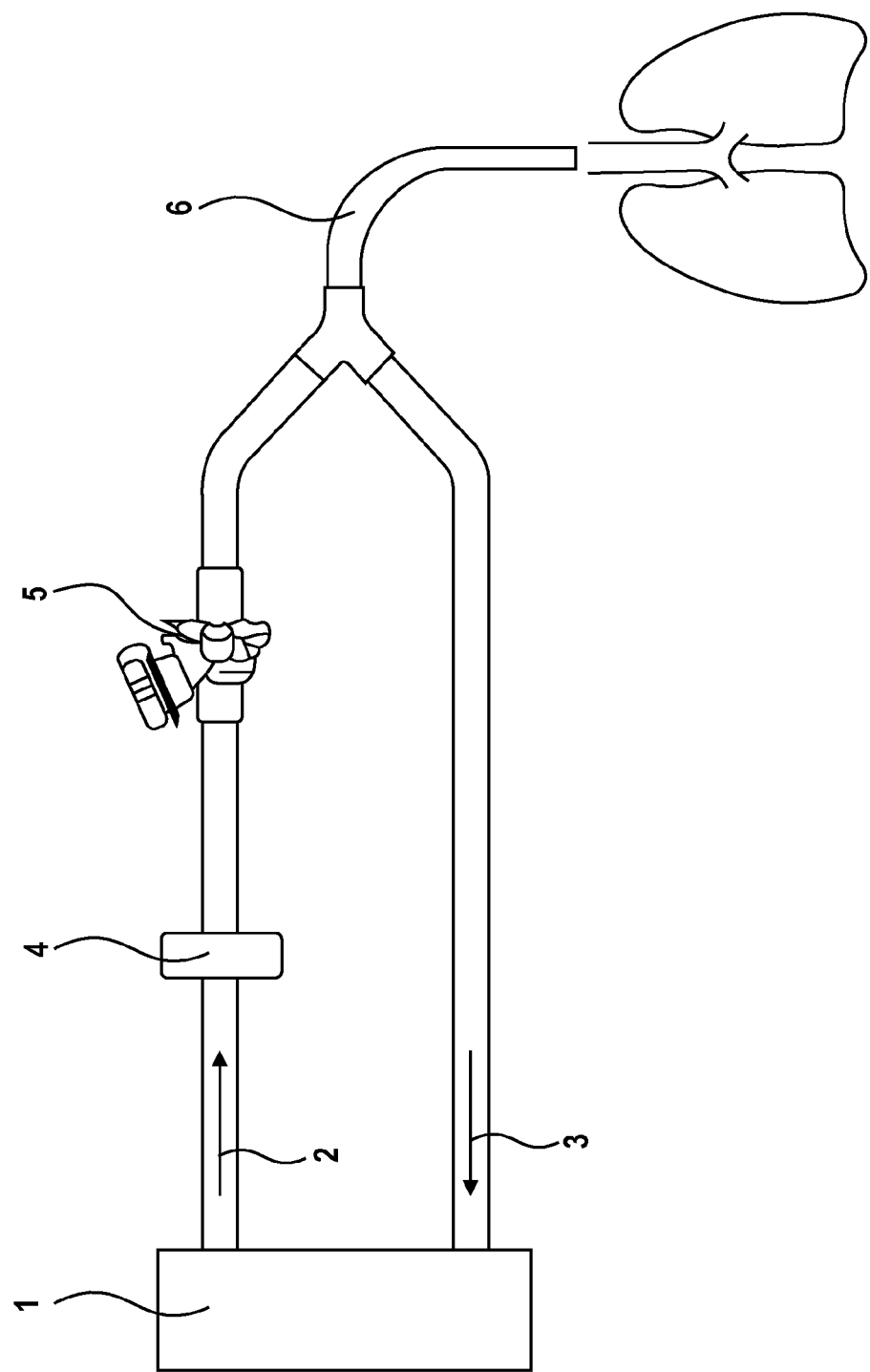

FORMULATIONS OF AMINOGLYCOSIDE AND FOSFOMYCIN COMBINATIONS AND METHODS AND SYSTEMS FOR TREATMENT OF VENTILATOR ASSOCIATED PNEUMONIA (VAP) AND VENTILATOR ASSOCIATED TRACHEAL (VAT) BRONCHITIS

CROSS REFERENCE TO RELATED APPLICATIONS

This application claims the benefit of U.S. Provisional Application No. 61/572,225 filed Jul. 12, 2011, which application is incorporated herein by reference.

BACKGROUND

Considerable medical literature and clinical experience establishes that ventilator associated pneumonia (VAP) is a feared and often fatal complication of mechanical ventilation. In the United States, over 250,000 patients are stricken with VAP per year or approximately 800 cases per million population. In Melbourne, the incidence has been reported in 2006 as 6.2 cases per 1,000 ventilator days, similar to the rate in the United States, Sogaard OS, et al. A binational cohort study of ventilator-associated pneumonia in Denmark and Australia. Scand J Infect Dis (2006); 38:256-264). The mortality of VAP averages 25%. Therefore, in patients with a poor prognosis, a VAP diagnosis is a life threatening complication. The onset and rapid progression to VAP usually occurs after 3-5 days of mechanical ventilation and starts with initial colonization of the airway with pathogenic bacteria. This is followed by a purulent tracheobronhitis (also known as ventilator associated tracheobronchitis (VAT) that rapidly progresses to VAP. VAT is considered a precursor to VAP. VAT is tracheobronchitis without new infiltrates on the chest radiograph (Nseir, Nosocomial tracheobronchitis Current Opinion in Infectious Diseases 2009,22:148-153). Not all VAT progresses to VAP, and not all VAP has had a precursor of VAT.

VAP also prolongs ICU stays and requires the use of intravenous antibiotics. However, the levels of antibiotics that can be achieved in the respiratory tract with intravenous administration are often lower than the therapeutic concentrations needed to treat the disease. Moreover, the continuing emergence of drug resistant organisms, particularly in hospital settings, makes this approach increasingly less effective. Specifically, the emergence of multidrug resistance bacteria such as methicillin resistant *Staphylococcus aureus* (MRSA), and Gram negative pathogens is increasing the morbidity of VAP.

Over the past twenty years, multiple investigator sponsored trials have attempted to study aerosolized antibiotics to either treat or prevent VAP. (See Palmer et al in Critical Care Medicine 2008; 36(7):2008-2013, Wood et al in Pharmacotherapy 2002; 22(8):972-982, and Lu et al in AJRCCM (Volume 184:106-115, 2011. Meta-analyses of these trials show benefit in decreasing ventilators days and improving other outcomes. Recently, Palmer and colleagues supra performed a randomized blinded placebo-controlled trial to determine with impact of aerosolized antibiotics on outcomes in patients with VAT and/or VAR Forty-three patients were randomized to receive aerosolized antibiotics or placebo for 14 days. Choice of aerosolized antibiotic was based on Gram stain of the endotracheal aspirate. Vancomycin or gentamycin were used in patients with Gram-positive and Gram-negative microorganisms, respectively. Both antibiotics were used if Gram-positive and Gram-negative microorganisms were present. Most of the 43 patients were also treated with systemic antibiotics. The authors found aerosolized antibiotics to be associated with significantly lower rates of VAP at the end of treatment, reduced usage of systemic antibiotics, and earlier weaning of patients from the ventilator leading to shorter stays in the ICU.

Palmer et al also showed the advantage of a cocktail of antibiotics, specifically gentamicin and vancomycin, that have gram negative and gram positive respective activity in treatment of VAP and VAT as many patients are infected with both gram negative and positive bacteria. Interestingly, lower rates of antimicrobial resistance were also found in patients treated with aerosolized antibiotics, likely as suboptimal levels, commonly seen with intravenous administration, are known to promote the development of bacterial resistance.

The delivery system used by Palmer and colleagues was a small particle size jet nebulizer, no longer manufactured, that introduced an additional 6 L/m airflow into the airway. Such a nebulizer is incompatible with many modern ventilators because modern ventilators have sophisticated control and feedback systems that carefully monitor and control airflow and pressures. A recent study by Lu, et al, compared ceftazidine and amikacin, aerosol (n=23) vs. IV (n=17) in a small Phase 2 trial in established gram negative bacteria and VAP. After 8 days of antibiotic administration; aerosol and intravenous groups were similar in terms of successful treatment (70% vs 55%), treatment failure (15% vs 30%), and superinfection by other microorganisms (15% vs 15%). Antibiotic resistance was observed exclusively in the intravenous group. The authors concluded that aerosol antibiotics have similar efficacy to IV and likely lead to lower rates of bacterial resistance.

The efficacy of aerosol adjunctive therapy or primary antibiotic treatment in VAP is not surprising. Intravenous antibiotics penetrate poorly into the sputum. Aerosol antibiotics generally have a 100 fold higher sputum concentration than maximum dose IV delivery with usually one tenth the systemic exposure. The rapid clearance from the respiratory tract of aerosol antibiotics leads to a situation of either very high concentrations or none, thus avoiding long periods of sub-MIC antibiotic concentrations which lead to the development of resistance. To date, no aerosolized antibiotics for VAP or VAT have been approved by regulatory authorities.

M promising combination of Gram-negative and Gram-positive antibiotics for VAT and VAP would be the combination of an aminoglycoside and fosfomycin. (Baker U.S. Pat. No. 7,943,118 and MacCleod J Antimicrobial Chemotherapy 2009;64:829-836). In patients with cystic fibrosis (CF) and *Pseudomonas aeruginosa* (a gram negative bacteria) infections, an 80 mg fosfomycin/20 mg tobramycin dose delivered twice daily as an aerosol by a vibrating plate nebulizer (PARI eFlow) was effective in decreasing the bacterial burden of *P. aeruginosa*, and *Staphylococus aureus* over a 28 day treatment period (Trapnell, et al. AJRCCM 185:171-178, 2012), Other aminoglycosides may also be synergistic with fosfomycin; Cai (J of Antimicrobial Chemotherapy 64 (2009) 563-566) reported that in both an in vitro and a systemically treated rat pseudomonas infection model, fosfomycin potentiated the efficacy of amikacin to even a greater extent than tobramycin.

The importance of an aerosol to be well tolerated is also well known in spontaneously breathing patients. While mild cough can be tolerated in a patient on a ventilator, coughing increases the airway pressures, putting the patient at risk for barotrauma. It is well known that hyperosmolar solutions for nebulization can cause cough. In fact, a 7% hypertonic saline solution having an osmolality of 2411 Osm/kg is used to induce cough to obtain sputum specimens or to promote airway clearance in patients spontaneously breathing with lung disease. Lower osmolality solutions still cause cough, a formulation of fosfomycin/tobramycin with a osmolality of approximately 1300 osm/kg when tested in CF patients can cause noticeable coughing in 10 to 41 patients while a placebo of normal saline (Osm/kg of 310) had coughing in only 3 of 40 patients. Wheezing, a more several measure of bronchospasm, occurred in 5 of 41 patients compared to none in the placebo group. (AMJ Respir Crit Car Med 185:171-178, 2012).

Therefore, although some combinations of antibiotics, including fosfomycin and aminoglycosides have been used, combinations for VAP and VAT have not been approved and several problems remain to be solved. First, ventilator circuits almost invariably include a humidifier to humidify the dry gas using sterile water coming from high pressure gas supplies prior to the gas entering the patient's airway. Humidification of the air leads to hydroscopic growth of the aerosol particles. Many particles grow to a size where they rain out in the endotracheal and ventilator tubing or, if delivered to the patient, deposit in the large airways. See Miller et all Am J Respir Crit Care Med 168:1205-09 (2003). An endotracheal tube's internal diameter averages 7-8 mm, much smaller than the diameter of a typical trachea. The smaller diameter increases "rain out" of large >5 micron particles such that those aerosol particles never reach the patient. The efficiency penalty of leaving the humidification circuit on with use of jet nebulizer with an average particle size of approximately 5 microns (at the nebulizer prior to growth due to humidification) has been estimated as loss of 50% of the aerosol. (Palmer et al in Critical Care Medicine 1998:26:31-38). To avoid this problem, the obvious solution is to turn off the humidifier during aerosol antibiotic therapy as was done in the treatment studies noted above (Palmer, Wood, Lu, Miller, supra). This is a successful approach but carries the finite risk of a health care worker neglecting to turn humidification back on. Accordingly, hospitals, critical care facilities and regulatory agencies would likely require specific warning devices because as non-humidified gas causes drying of secretions that make recovery from pneumonia even more difficult. A method that allows continuous humidification is optimal and would increase patient safety and treatment efficacy.

Second, improved airway tolerance is needed for patients with VAT and VAP. In the recent study of Lu, et al, it was a common occurrence for the patient to breath out of sequence from the ventilator, likely caused by irritation from the therapeutic aerosol. Eschenbacher (Eschenbacher et al, Am Rev Respir Dis 1984; 129: 211-215) published that mild asthmatic patients will cough when exposed to an aerosol without a permeant anion such as chloride at a concentration of greater than 20 meq/liter even if the aerosol is isotonic. Lu utilized sterile water to reconstitute the powdered antibiotics and did not use any saline in his formulation which would provide a permeant anion. Lu's approach was to heavily sedate the patient, which is not optimal.

Third, Eschenbacher (supra) tested a hypertonic saline solution of 1232 mOsm/liter and showed in mild asthmatic patients that cough and bronchospasm were common. Pretreatment with bronchodilators could prevent bronchospasm, but could not prevent cough. As noted above, coughing on the ventilator is not desirable, as it can cause high airway pressures leading to pneumothorax, or interfere with delivery of adequate ventilation. The osmolality of a fosfomycin/tobramycin combination currently being used in clinical studies of outpatient CF patients is approximately 1215 mOsm/liter, far above the physiologic airway osmolality of approximately 310 mOsm/liter. The high osmolality is due to the low MW of fosfomcyin, coupled with the fact that it is a disodium salt. The disodium salt of fosfomycin has a solubility of 50 mg/mL of water, other salts including calcium are available but have less solubility concentrated formulations are not practical. The high osmolality formulation is used so that each dose can be delivered in a 2 mL solution in a vibrating mesh nebulizer so treatment time for a CF outpatient is approximately 5 minutes. More dilute solutions would require longer administration times which lead to poor compliance and potentially less efficacy. Higher osmotic concentrations have larger hydroscopic growth. Thus, if such formulations were used in a ventilator, a large amount of >5 micron particles would rain out in the tubing, and the remaining amount that was delivered would likely be irritating to the airways. A common adverse event of cough was reported in the phase 2 CF study. In fact the high dose (160 mg, fosfomycin/40 ma tobramycin, same osmolallty in a 4 mL solution) was very poorly tolerated in the CF study in spite of all the patients pretreated with a bronchodilator to prevent bronchospasm.

Fourth, the epidemiology of resistance and goals of therapy are very different in VAP and VAT compared to outpatient CF. However, in the hospital setting, once bacterial resistance occurs, the spread of resistant bacteria between patients is rampant and epidemics are common. Furthermore, the risk of aminoglycoside toxicity from the cumulative long-term dose( ) is serious because CF patients are treated chronically for years with tobramycin aerosols. In contrast, in VAT and in VAP, a patient is likely to only receive a single, two week course of antibiotics. Therefore, when used to treat VAP or VAT, limiting a dose of an aminoglycoside in a combination product, and relying on fosfomcyin to increase bacterial killing, risks the loss of efficacy of both drugs if a patient has bacteria that are fosfomycin resistant. For example, in contrast with high ratios of Fosfomycin to Tobramycin disclosed in Baker '118, an optimal formulation in VAP and VAT would have enough of an aminoglycoside dose to be an independently effective antibiotic combination. However this approach would only increase the osmolality of the formulation if the volume of the formulation is held constant. The advantage of the fosfomycin would be to further enhance gram negative killing, including biofilms (Cai, supra) and to also treat gram positive bacteria, including methicillin resistant *Staph. aureus* (MRSA). Another advantage of fosfomycin is that it reverses some of the sputum antagonism that limits the bioavailability of aminoglycosides (MacCleod, supra), (Mendelman Am Rev Rispir Dis 1985;132:761-5). Thus, even if the bacteria is fosfomycin resistance, there may be some clinical benefit to the combination by increasing the bioactive concentrations of the aminoglycoside.

One solution would be to dilute out the formulations and increase the volume placed in the nebulizer for treatment. However, observation of a patient during therapy would then likely to be required as standard protocol. ICU specialist nurses or respiratory therapists would likely be required to observe the patient during treatment adding an additional costs to the therapy due to the prolonged administration time. Serious adverse events can occur during aerosol therapy, such as in Lu's study, where a patient had a cardiopulmonary arrest due to a clogged exhalation filter on the ventilator. An optimal formulation would have shorter delivery time than that of a dilute formula. Triggering the delivery during inspiration would extend treatment time but the time loss may be offset by improvement in the efficiency of delivery. Thus, a need for a treatment protocol exists wherein lower doses may be evaluated.

Accordingly, a need exists for antibiotic compositions, equipment, and treatment methods and systems to alleviate or prevent VAT and VAP despite the known challenges and the recognized risks.

SUMMARY OF THE INVENTION

The present invention is improved formulation of an aminoglycoside and fosfomycin in combinations, systems, and methods for the treatment, alleviation and prevention of ventilator associated pneumonia (VAP) and ventilator associated tracheal (VAT) bronchitis. The antibiotic compositions of the invention include combinations of amikacin and fosfomycin combined in a hypertonic solution having specific ratios, concentrations of permeant ion, including specifically chloride ion, pH ranges, particle sizes in an aerosol mist and levels of osmolality designed to further the therapeutic goals of the invention. These physical and chemical parameters are uniquely selected to enhance the bacteriacidal performance of the combination in the ventilator-based and nebulizer-based modes of administration. Specifically, the ratios of amikacin to fosfomycin are greater than 1:1 and preferably greater than 2.5-2.6:1.0. The pH range is generally between about 4.4 and 7.5 and preferably between 6.9 and 7.4. The concentration of permeant and ion is greater than 30 equivalents per liter and, in some formulations, greater than 40 milliequivalents per liter. The osmolality is greater than 300-310 milliosm/L and less than about 800 milliosm/L and generally less than 1,000 milliosm/L. The concentration of the first and second antibiotic component are both, individually and synergistically in combination, bactericidal, and preferably have a quantity greater than MIC 90 for a target organism. The aerosol can be formed from a solution containing any low molecular weight drug that requires high concentrations for efficacy, or cations or anions of such drugs having an osmolality that is higher than desired for tolerance upon aerosol administration. In certain embodiments described below, the antibiotic components may be either liquids, solids, or formulated as aerosols or dry powders and may be any physiologically compatible salt of the compositions described herein.

The first component of the antibiotic combination and composition is amikacin, a well-known and widely used aminoglycoside having activity against Gram negative organisms. Although amikacin is not approved for aerosol use, it has been used in multiple VAP studies as a regimen component that includes either standard IV drugs or ceftazidine aerosol, Niederman, et al. NKTR-061 (Inhaled Amikacin) Reduces intravenous Antibioitc Use in Intubated Mechanically Ventilated Patients During Treatment of Gram-Negative Pneumonia( ) from 27th International Symposium on Intensive Care and Emergency Medicine Brussels, Belgium. 27-30 Mar. 2007 Critical Care 2007, 11 (Suppl 2):P97, 5; Lu Q, et al. Nebulized ceftazidime and amikacin in ventilator-associated pneumonia caused by *Pseudomonas aeruginosa* in AJRCCM Articles in Press. Published on Apr. 7, 2011 as doi: 10.1164Irccm.201011-1894OC). Systemic exposure is low with aerosolized amikacin and thus safer than intravenous administration in regards to renal toxicity. A data base of greater than 15,000 hospital pathogens was recently published and represents current resistance data after a generation of amikacin use. Zhanel G G, et al. Antimicrobial susceptibility of 15,644 pathogens from Canadian Hospitals: results of the CANWARD 2007-2009 study. Diagnostic Microbiology and Infectious Disease 69 (2011) 291-306). The MIC 90 (the minimal inhibitory concentration of 90% of the isolates) was 32 ug/mL for Pseudomonas. In all other Gram negatives with the exception of *Stenotrophomonas maltophilia*, the MIC 90 was lower. The MIC 90 of *S. maltophilia* was >64 ug/mL. The limitations of amikacin are that its activity against MRSA is limited, and activity against Gram negative bacteria in biofilms is poor.

The second antibiotic component of the drug formulation is fosfomycin, a broad spectrum phosphonic acid antibiotic that has both Gram positive and negative activity. Fosfomycin oral monotherapy is commonly used to treat uncomplicated urinary tract infections. Recently fosfomycin was proven to be safe and effective as an aerosol in combination with tobramycin in treating CF patients with pseudomonas infections, Trapnell B C,et al Fosfomycin/Trobramycin for Inhalation (FTI): Efficacy Results of a Phase 2 Placebo controlled Trial in Patients with Cystic Fibrosis and *Pseudomonas aeruginosa*. Poster 233 24th Annual North American Cystic Fibrosis Conference, Oct. 21-23, 2010, Baltimore Md., Trapnell B C, et al Fosfomycin/Tobramycin for Inhalation (FTI): Safety Results of a Phase 2 lacebo controlled Trial in Patients with Cystic Fibrosis and *Pseudomonas aeruginosa*. Poster 234 24th Annual North American Cystic Fibrosis Conference, Oct. 21-23, 2010, Baltimore Md.). In addition, it was effective in treating MRSA that was seen as a coinfection in approximately ⅓ of the treated patients. The antibiotic's efficacy with amikacin is superior to what is seen with tobramycin. Cai, et al, reported that fosfomycin in vitro increased the activity in vitro of amikacin by a factor if 64, and in a rat biofilm pseudomonas infection model the combination of fosfomycin and amikacin improved efficacy compared to monotherapy of either component Cai Y, et al. Synergistic effects of aminoglycosides and fosfomycin on *Pseudomonas aeruginosa* in vitro and biofilm infections in a rat model. J of Antimicrobial Chemotherapy 64 (2009) 563-566). Fosfomycin is not used in North America as an IV antibiotic and there is no recent data on fosfomycin MIC's from MRSA. However, data from the 1980s reports an MIC90 of 32 ug/mL. Alvarez S, et al., In Vitro activity of Fosfomycin, Alone and in Combination, against Methicillin-Resistant *Staphylococcus aureus*. Antimicrobial Agents and Chemotherapy 28 (1985) 689-690). With little general use, one would expect similar values today.

In one embodiment, the combined formulation will be a neutral pH hypertonic solution of at least about 50 mg/mL of amikacin, and at least about 20 mg/mL of fosfomycin with at least 30 equil/L of Chloride anion. The osmolality of this formulation will be approximately 700 milliosm/L, and with dilution from the humidification from the ventilator circuit, the final osmolality will be approximately 425 milliosm/L. Normal airway osmolality is 310 milliosm/L and mildly hypertonic solutions are well tolerated by patients. The use of a permeant anion is to prevent cough in patients with mild asthma and is used in approved aerosol antibiotic formulations such as tobramycin solution for inhalation and aztreonam for inhalation, Eschenbacher W L. Alteration in Osmolarity of Inhaled Aerosols Cause Bronchoconstriction and Cough, but Absence of a Permeant Anion Causes Cough Alone. Am Rev Respir Cis (1984); 129:211-215), The peak concentrations that one can achieve in the sputum can be predicted by estimating the mass of drug delivered to the lower airways in mg and multiplying by a factor of 30 to get an estimate of ug/mL concentrations. For instance for TOBI, 36 mg is delivered to the lung and the sputum concentrations are approximately 1,000 ug/mL. For Cayston, 30 mg is delivered and the concentrations are approximately 750 ug/mL.

About 75 mg of amikacin and about 30 mg of Fosfomycin are delivered to the lung if a 10 mL dose is used in a nebulizer with at an expected 15% delivery efficiency. The predicted concentrations of amikacin would be about 2250 ug/mL, greater than 25 times the MIC90 for most Gram negative organisms. The predicted peak concentrations of fosfomycin would be about 900 ug/mL, again greater than 25 times greater than the MIC90 for *Staph aureus*. This prediction is based on the similar ratios of deposited drug (in mg) to sputum concentrations in ug/mL that is seen with tobramycin and aztreonam aerosols. With the exception of pentamidine that has a prolonged half life in the lung due to binding of the drug to surfactant in the alveolar space, the two other FDA approved inhaled antibiotics; tobramycin and aztreonam have an airway half life of about 2 hours. Thus, dosing for aerosolized antibiotics is generally bid or tid as there is little therapeutic drug remaining after 5 half lives or ten hours. Systemic absorption of deposited drug is about 10%, thus, even with sputum concentrations on average 100 fold greater than what can be achieved with intravenous drug, the systemic exposure of aerosol antibiotics is in the range of 10% of a therapeutic intravenous dose.

Peak concentrations are not a perfect predictor of efficacy. In the case of amikacin, sputum is known to antagonize the bioavailability of amikacin and thus doses that achieve at least 10 fold the MIC90 fold higher are needed for efficacy, Mendelman et al., Aminoglycoside penetration, in activation, and efficacy in cystic fibrosis sputum. Am Rev Respir Dis (1984); 132:761-765), Efficacy is also known to be correlated with peak concentrations of aminoglycosides, making aerosol delivery with the high concentrations nearly ideal. In the case of fosfomycin, time above the MIC is more important than peak concentrations. The half-life of inhaled aerosol is on average approximately 2 hours, so a 900 ug/mL initial does would be at the MIC90 of MRSA after 6 half-lives or about 12 hours.

Twice daily dosing is preferred due to the rapid clearance of fosfomycin, and prior study data from aminoglycoside treatment. In a Phase 2 VAP study comparing once a day versus twice a day aerosolized amikacin as adjunctive therapy to IV antibiotics, twice a day was superior in reducing the need for additional salvage antibiotics. Niederman, et al. NKTR-061 (Inhaled Amikacin) Reduces Intravenous Antibioitc Use in Intubated Mechanically Ventilated Patients During Treatment of Gram-Negative Pneumonia, (27th International Symposium on Intensive Care and Emergency Medicine Brussels, Belgium. 27-30 Mar. 2007 Critical Care 2007, 11 (Suppl 2):P97). Uniquely challenging bacterial infections subject to treatment by the compositions of the invention are organisms that are drug resistant, such as MRSA, and those harboring genes that confer bacterial resistance. In particular, genes encoding the carbapenamase enzymes. These beta lactamase enzymes confer resistance to beta lactam antibiotics by hydrolyzation of carbapenems, The New Dehli metallo-beta-lactamase-1 (NDM-1) is a class B metallo-beta-lactamase that has spread worldwide and is frequently associated with so-called super bugs due to the rapid spread and resistance to antibiotics conferred by the enzyme. Genes encoding NDM-1 or other carbapenamases can be exchanged between organism by a variety of methods including conjugation, plasmid exchange, bacteriophage transduction and others. The genes can be incorporated in the chromosomes or borne by a plasmid. Treatment by the methods and compositions of the invention may follow identification of a carbapenamase in a bacterial isolate or by any standard methodology that establishes bacterial resistance. Accordingly, the methods of the invention include administering the compositions and utilizing the methods described herein in response to identification of a resistant organism.

An ideal aerosol delivery system for existing mechanical ventilators would have the following parameters: the system would be compatible with all ventilator models made of disposable components, capable of creating small particle aerosol size to prevent rainout in the endotracheal tube, and capable of rapid delivery of therapeutic quantities of antibiotic without creating additional airflow to trigger ventilator alarm or control systems. A nebulizer with these parameters, the PARI e-Flow in-line nebulizer, yields the data disclosed herein. By vibrating a laser drilled thin stainless steel membrane, a small nearly uniform small particle aerosol is created for drug delivery. This technology has been proven in the handheld Altera® device recently approved to deliver aztreonam for inhalation in patients with cystic fibrosis with chronic endobronchial pseudomonas infections. A similar membrane, modified by a smaller hole size and located in a unit that is placed in-line with a ventilator inspiratory tubing is preferred. The design is unique with the membrane in the middle of the tubing, with the inspiratory flow freely moving around the membrane to entrain the aerosol as it is created (See FIG. 1). The nebulizer will be run continuously, and the estimated lung deposition is 15%. Bias flow, if a feature on the ventilator, will need to adjusted to less than 5 Liters/minute to prevent excess flushing of the drug during exhalation.

FIG. 1 is a schematic of a system of the present invention comprised of a complete airway including a ventilator 1, inspiratory 2 and expiratory limbs 3, a humidifier 4, an in-line nebulizer 5 and fixture 6 for operably connecting the system to a patient. The position of the humidifier 4 is preferably proximate to the in-line nebulizer 5 and the nebulizer 5 is most proximate to the patient. The humidifier 4 and the nebulizer 5 are both joined to the airway of the ventilator by a fixture that is sealed at each point of attachment to the inspiratory limb 2 such that additional air is not introduced into the inspiratory limb 2 during inspiration by the patient. The antibacterial composition yielding a hypertonic solution is introduced into the nebulizer 5 for administration to the patient. Unlike drug administration protocols provided in the medical literature, the humidifier 4 is affirmatively activated during operation of the nebulizer 5 to achieve the method for reducing the osmolality of hypertonic solution as described above. As noted above, the humidifier 4 and/or the nebulizer may be activated by program, by patient inspiration or may be continuous during administration of the drug.

Because humidification does not need to be turned off during delivery, the small particles grow to an average size of about 3.2 microns after humidification, leading to excellent peripheral deposition. The nebulizer is designed to be in line for the entire treatment course. The electronic control unit, the size of a cell phone, is plugged into the wall outlet with a cord that attaches to the nebulizer. The nebulizer would be inserted near the distal end of the inspiratory tubing to work with any positive pressure ventilator. Unlike a jet aerosol device, it would not introduce any additional air to avoid hyperinflation or barotraumas in a patient. The disposable drug/device components eliminate the cost of cleaning, and reduce the risk of bacterial contamination of a nebulizer, a known source of nosocomial infection. In addition, a single patient use prevents any risk of patient to patient transmission of resistant bacteria. Drug delivery time would likely be approximately twenty minutes, twice a day.

In the methods of the present invention, a combination of amikacin and fosfomycin are administered at a ratio of amikacin to fosfomvcin greater than 1.1, and preferably greater than or equal to 2.6:1. The combination of antibiotics is dissolved in a hypertonic solution as described above and is used to create an aerosol mist having a mean particle size less than five microns and an osmolality less than a 1000 milliosm/L. The combination is preferably delivered by placing each in a reservoir in the in-line nebulizer located within the airway of a mechanical ventilator. Alternatively, either component may be delivered by attaching a drug reservoir such as a dry powder container at a point where inspiration by the patient or movement of air in the ventilator airway advance drug composition to the patient. Preferably, the nebulizer is sealed in the airway to prevent additional airflow from being introduced and to permit a combination of the aerosol mist of the antibiotic formulation with humidified air generated by the ventilator system. In the system described herein, movement of air through the pathway of the ventilator combines humidified air and the aerosol mist containing the antibiotic formulation and may be triggered by patient inspiration or as part of a continuous or programmed delivery protocol such that the nebulizer is in intermittent or continuous operation during the administration of the antibiotic combination. In each case, the formation of the aerosol maintained for a duration adequate to deliver bacteriacidal amounts of the antibiotic combination to the lung of the patient.

The calculation of the total antibiotic delivery may be achieved by the quantity of the antibiotic, bactericidal dose, such as the MIC 90 for any identified organism or may be determined through clinical observation of the organism. As described in connection with FIGS. 1 and 2 below, the ventilator system typically has an airway that extends from the pressure generating components of the ventilator through the airway and into the wye fixture that terminates at the patient. The in-line nebulizer may be placed at any point in the airway between the positive pressure generating mechanics and the patient, however the placement of the nebulizer proximate to the patient near the ventilator wye piece is preferred. The nebulizer and the humidification apparatus of the ventilator should be oriented so that the humidified air causes hygroscopic growth of the individual particles in the aerosol mist. As noted elsewhere herein, the advantageous expansion of the aerosol mist particles from an initial size to an enlarged size, caused by the humidification effect on the radius of each particle, will dictate the location of the nebulizer and the humidification apparatus. The combination of the humidified air and the antibiotic solution mist must also achieve reduction in the osmolality as described herein.

In practice, a patient is connected to a ventilator for breathing assistance and the ventilator system is adjusted to provide for a continuous and controlled airflow based on known physiological parameters. The antibiotic composition of the invention is introduced into a reservoir in the nebulizer and is stored therein until delivery. To administer the antibiotic combination of the present invention, the in-line nebulizer is connected to the airway of the ventilator and activated to create the aerosol mist. Upon delivery, the nebulizer generates the aerosol mist from a vibrating apparatus disposed therein, typically a vibrating mesh or membrane that has numerous apertures formed therein to produce particles of a defined size from solution. The humidification generator is activated and maintained in operation during each delivery of the aerosol mist formed from the hypertonic solution such that the osmolar load is reduced. Thus, the advantage of an inline nebulizer as described herein is to permit the humidified air in the ventilation airway to pass through the nebulizer and to combine with the aerosolized portion of the hypertonic antibiotic combination solution.

Although the embodiment for treatment of VAP and VAT are described herein in the context of a treatment that occurs while a patient is connected to a mechanical ventilator system, the compositions of the present invention are suitable for administration to a patient who has been removed from a mechanical ventilator but continues to suffer a bacterial infection, typically as a result of the aftermath of a diagnosed VAP or VAT condition. In such cases, the antibiotic composition of the present invention can be delivered through an ordinary nebulizer as in the case of antibiotics delivered to patients suffering from cystic fibrosis. In such circumstances, the total composition of the administered antibiotic, the formulation parameters, and all other characteristics of a bacteriacidal treatment regimen are maintained.

DESCRIPTION OF THE FIGURES

FIG. 1 is a schematic of a ventilator and in-line nebulizer configured to deliver the compositions and perform the methods of the present invention.

DETAILED DESCRIPTION OF THE INVENTION

The estimated therapeutic doses of aminoglycoside and fosfomcyin can be determined by examining the literature. For tobramycin, the drug TOBI has a 300 mg nebulizer dose with an estimated lung delivery of 12% or about 36 mg delivered dose in spontaneously breathing CF patients infected with *pseudomonas*. Similarly delivery was shown by Clark et al (Evaluation of the Disposition and Safety of Tobramycin Solution for Inhalation in Ventilator-Associated Pneumonia or Tracheobronchitis Patients R. Clark, MD, L. Heslet, MD, PhD, K. Antonsen, MD and B. Donehower, Pharm D. ATS 2003 Seattle, Wash. 99th International Conference) in patients on ventilators with a jet nebulizer. Sputum concentrations are close to 750 ug/gm sputum, which is 10 times greater than MIC90 of 64, the MIC90 (minimal inhibitory concentration of the tested antibiotic for the lower 90% of isolates in a survey of isolates from patients) of most *pseudomonas* isolates.

Amikacin is a preferred aminoglycoside in the ICUs and in ventilator patients due to its better activity against Acinetobacter bacteria than tobramycin. In aerosol studies, a nebulizer dose of 400 mg amikacin with up to 70% efficiency of delivery for a total dose of up to 250 mg to the lung has been used. Sputum concentrations are in the 6,000 ug/mL range (Niederman et al, BAY 41-6551 (Inhaled Amikacin) achieves bactericidal_tracheal aspirate concentrations in mechanically ventilated patients with gram-negative pneumonia (Intensive Care Medicine 38:263-271, 2012) A Pharmacokinetic Study ATS 2010 New Orleans, La.). The vibrating plate nebulizer used in this study triggered only on inspiration resulting in a delivery efficiency of about 70%, If run continuously, a vibrating plate nebulizer has about 15% delivery efficiency (Hahn et al In vitro assessment of a novel nebulizer for mechanically ventilated patients based on the eFlow technology, ISAM 2009, Monterey Calif.). In the phase 2 CF fosfomycin/tobramycin study, the nebulizer dose of tobramycin was only 20 mg, with estimated 5 mg delivered to the lung. This illustrates the synergy seen with the combination but as noted before, relying on the synergy may not be appropriate in VAP (a life threatening disease) in patients with bacteria that are resistant to fosfomycin.

The doses of aminoglycosides at first examination seem excessive, however it is well know that sputum macromolecules bind aminoglycosides so up to 90% of aminoglycoside is bound and therefore inactive. Therefore, with aerosol aminoglycoside monotherapy, a sputum concentration that is a least 10 fold higher than the MIC90 is considered necessary, and higher fold concentrations, up to 25 fold may provide increased bacterial killing (Mendelman Am Rev Rispir Dis 1985;132:761-5). Fosfomycin interferes with the sputum antagonism, (MacCleod, supra), thus even if the bacteria are fosfomycin resistant, there may be some clinical benefit to the combination by increasing the bioactive concentrations of the aminoglycoside.

The optimally effective dose of fosfomycin is likely at least 20 mg delivered to the lung, with nebulizer doses of ranging from 30 to 100 mg depending on nebulizer efficiency. This is based from the successful phase 2 CF trial (Trapnell et al, supra) showed decreased bacterial density of both pseudomonas and *Staphylococcus aureus* in the subset of patients who were co-infected, with approximately 20 mg delivered to the lung. In this trial an estimated 40 mg delivered dose of fosfomcyin was more efficacious in killing *staphylococcus* than the estimated 20 mg dose, showing that a higher dose may be better. The fosfomycin salt that is most soluble is the disodium salt and is preferable. Another soluble salt is fosfomycin tromethamine, other salts are possible such as calcium.

The recent development of vibrating plate nebulizers, particularly one by PARI, enable particle sizes less than 5 microns. See WO 2005/045982A2. Membranes having a plurality of small apertures therein can produce mean particle sizes less than 5 microns and in the range of 3.5 microns. This is accomplished by making the porous holes smaller in the laser drilling process. Other vibrating plate membranes by PARI have a 4.5 micron average size particle as does the vibrating plate nebulizer introduced by Aerogen/Nektar. Similarly, there are small particle jet nebulizers that can produce 2 3 micron size particles. Current ultrasonic nebulizers produce an average particle size of 5 microns using a 2.7 MHtz driving frequecncy. Ultrasonic nebulizers can create smaller particles by increasing the frequency of the ultrasonic generator; no high frequency (2.3 Mhtz) are currently commercially available in the United States or Europe at this time, but they would have a 2-3 micron particle size. In addition, ultrasonic nebulizers heat the nebulizer solution and this may lead to drug degradation during therapy, for this reason, their use has fallen out of favor.

The present invention includes the use of humidification as a technique to improve the tolerability of hypertonic solutions delivered as an aerosol. The creation of an aerosol with a small particle size from a hypertonic solution can produce a composition of small particles that carry a desirable therapeutic dose but are poorly tolerated due to a high osmolality on the order of three fold or greater of normal osmolality, (e.g. ≥930 mOsm/kg). Adding humidification to the aerosol yields an aerosol composition that has a reduced osmolality and is preferably close to isotonic or less than two fold normal osmolality (e.g. <620 mOsm/kg). The humidification is created by an in line humidifier to preferably decrease the osmolality to a range from greater than three fold to less than two fold normal osmoltiy and may vary depending on the nature of the original hypertonic solution, the particle size of non-humidified aerosol as hydroscopic growth of a 4 micron particle may lead to much more dilution that a growth of sub 3 micron particle. In such hypertonic solutions, the permanent ion in solution is preferably greater than 4 0 mequil/L. For such a method, the humidification can be applied to aerosols formed from a variety of hypertonic solutions where paired tolerability is desired. Examples include any small molecular weight drugs that require high concentrations for efficacy, or compounds that are salts with multiple anions or cations that create a high osmolar load in a solution.

In the aspect of the invention below, aminoglycoside/fosfomcyin combinations are hypertonic on administration but close to isotonic upon delivery by the advantage of increased humidification compared to ambient air. For instance, if the particle size grows on average from 3.5 to 4.5 microns, the dilution of the contents is a function of the cube of the radius or 4.91/11.3. Therefore, the use of small particle aerosol with subsequent hydroscopic growth due to humidification would substantially reduce the osmotic load on the lung. With a larger initial particle size, the effect would be similar. For example, the growth from a 5 to 6 micron particle would lead to a dilution of 15.6/27. If particles are allowed to grow much larger than 5 microns, tolerability is not the primary issue as little will be deposited in the airways due to rain out in the ventilator and endotracheal tubing. This was shown in the seminal studies by Palmer (supra) on the deleterious effect of humidification on total drug delivery. These studies mostly utilized jet nebulizers that have an average of 4-5 micron particles prior to growth due to humidification, the hydroscopic growth was responsible for rain out and less drug delivered to the airways. For instance the ratio of 4.91/11.3, if a hypertonic solution is used with a nebulizer that has a 3.5 micron average particle, an osmolality of up to 710 would become on average isotonic. Slightly hypertonic formulations can be tolerated by the lung, it is likely a formulation with an osmolality of up to 800 would be well tolerated by the humidification technique.

The PARI in-line nebulizer designed for ventilator use can be outfitted with a small pores membrane and has a current volume capacity of 10 mL, and a rate of delivery of 0.0.5-0.0.6 ml./minute. Although it is currently not configured for triggering on inspiration, a nebulizer may be so configured when operably connected to the control system of the ventilator. Particle size would be estimated at 3.2 microns. A formulation of 10 mL, with 100 to 300 mg Fosfomycin and 300 to 600 mg of amikacin at the 15% efficiency rate would provide adequate killing for *Staphylococcus aureus* and Pseudomonas. An ideal formulation would contain at least 20 meq/l of chloride anion after dilution. The estimated osmolality of a solution of 50 mg/mL amikacin and 20 mg/mL of fosfomycin, with chloride anion, adjusted to a pH between 4.5 and 7.5 is approximately 750-850 osm/L. If diluted by humidification, this would likely be close to the isotonic range when deposited in the airways. To vary the delivered dose, a smaller or larger volume could be used, or alternatively or in combination, trigger delivery on inspiration phase of breathing to increase the deposition amount.

EXAMPLE #1

Preparation of Fosfomycin/Amikacin Solution for Aerosolization

A fosfomycin/amikacin solution having a ratio of 2.6:1 may be prepared as follows: Fosfomycin disodium (12.90 g, 10.00 g free acid) was dissolved in 250 mL of water and the pH was adjusted to 7.41 by the dropwise addition of 4.5 N HCl (estimated 1 mL). To the resulting solution was added 25 gm Amikacin base. The pH of the solution was adjusted to 7.60 by the addition of 4.5 N HCl (total amount of 4.5 N HCl was 1.7 mL). The solution was diluted to 500 mL with water and filtered through a 0.2 micron Nalge Nunc 167-0020 membrane filter for sterility. The chloride content can be calculated by using 1.7 mL of 4.5N HC in 50 L total for a total 306 mg chloride. As 1 mEq Cl=35.5 mg in 1 L then in 50 mL 1 mEq Cl=1.775 mg. Therefore, 306 mg/1.775 mg=172.4 mEq/L. The osmolality of this formulation was measured at 592 mOsm/kg which is above the normal physiologic value of 310 mOsm.

EXAMPLE #2

Reduction of the Osmolality of the Solution by Humidification

The 2.6:1 Fosfomycin/Amikacin Solution was prepared as above. Using an inline electronic vibrating late nebulizer (PARI, Sternberg Oreg.), the formulation was nebulized in dry (4%) and humid (100%) humidity. The mean particle size, as measured Malvern X laser particle sizer was 2.9 μm under dry conditions, increasing to 3.2 μm under 100% humidity.

Since the volume of a sphere is a function of the third power of the radius, the following equation yields the dilution factor.

1.45×1.45×1.45=0.75

1.6×1.6×1.6

Thus the formulation on average is diluted by a factor of 0.75, indicating the delivered formulation has an osmolality of 592×0.75=444 mOsm/Kg.

EXAMPLE #3

Randomized, Double-Blind, Placebo Controlled, Dose Esclation Phase 1b Study of Aerosolized Amikacin and Fosfomycin Delivered Via the PARI Investigational eFlow® Inline Nebulizer System in Mechanically Ventilated Patients A dry powder fosfomycin, liquid amikacin solution can be prepared by use of 200 mg neat dry powder disodium fosfomycin filled in glass vial or two part dry liquid syringe. In either a separate syringe, blow fill seal container, or a two part syringe, 500 mg of amikacin base dissolved in 10 mL of sterile water, with the pH adjusted to a range of 4.5 to 7.5 with HCl. The two components are then mixed together giving a solution with 20 mg/mL fosfomycin, 50 mg/ML amikacin. The osmolality of the solution would be approximately 600 mOsm/Kg, but could vary up to 10% depending on the amount of HCl used to adjust the pH of the amikacin solution.

A treatment was designed to contain safety, efficiency, tolerability and to further elucidate systemic and tracheal aspirate pharmacokinetics of nebulized amikacin/fosfomycin in patients with a clinical diagnosis of VAP or VAT following delivery of 2 mL, 4 mL, 6 mL, 8 mL, 10 mL and 12 mL doses via the PARI Investigational eFlow® Inline Nebulizer System in mechanically ventilated patients.

The combination antibiotic amikacin/fosfomycin (50 mg/mL amikacin and 20 mg/mL fosfomycin) was delivered via the PARI Investigational eFlow® Inline Nebulizer System in mechanically ventilated patients. A placebo: 0.9% normal saline, having a volume matched to the antibiotic dosing schedule was delivered via the PARI Investigational eFlow® Inline Nebulizer System in mechanically ventilated patients.

The eFlow® Inline Nebulizer System was positioned in the inspiratory tubing between the Puritan Bennett 840 Ventilator and the patient. Once in place, the nebulizer remained in-line until all study drug doses were delivered. Humidification continued during the nebulization of the formulation and the delivery of the entire dose.

Patients are male or female between 18 years and 80 years of age with clinical diagnosis of VAP or VAT, a Gram positive or Gram negative bacteria on Gram stain of the tracheal aspirate and were expected to be on mechanical ventilation for at least three days.

Study Duration: With a maximum screening period of one day, a three day treatment period, and follow up 24-hours following dosing with Investigational Product, the maximum study duration is five days.

Pharmacokinetic Parameters: Analysis of amikacin and fosfomycin systemic concentrations at pre-dose, 10 minutes, 1, 2, 4, 6 and 24 (±2) hours post dosing.

One patient has completed the trial. No adverse respiratory events were noted during or after study drug administration. Peak and plateau airway pressures did not increase in a clinical significant amount. No oxygen desaturation was noted. The humidification of ventilator circuit with the use of a hypertonic formulation resulted in a safe administration to a patient.

EXAMPLE #4

Clinical Study for VAT/VAP

A GLP (Good Laboratory Practice) study (was performed using twenty four beagle dogs allocated to four dose groups (three males and three females per group) and exposed to aerosol generated with the PARI Investigational eFlow Inline Nebulizer System using a closed-faced mask fitted with a mouth tube. The aerosols contained either control (water for injection) in Group 1 or a combined formulation containing 50 mg/mL amikacin and 20 mg/mL fosfomycin pH adjusted with HCl for Groups 2 to 4. Aerosol concentrations were determined on Days 1 and 7. The treatment period was for seven days with termination of the dogs on Day 8. The average daily achieved dose of amikacin:fosfomycin for each group was 32.1:12.4 mg/kg/day (a 2.59:1 ratio) (Group 2); 63.0:24.7 mg/kg/day (92.55:1 ratio) (Group 3); and 116.8:47.5 mg/kg/day (92.46:1 ratio) (Group 4). The highest estimated pulmonary dose was 29.2 mg/kg/day amikacin and 11.9 mg/kg/day fosfomycin. The particle size distribution (MMAD [Mass Median Diameter]) based on analytical methods was determined to be respirable averaging 2.80 μm (GSD=1.778) for amikacin and 2.75 μm (GSD=1.670) for fosfomycin.

The aerosol was well tolerated by all dogs. There were no treatment-related adverse effects based on clinical observations, body weights, food consumption, ophthalmoscopy, or electrocardiography. Any changes to clinical pathology values observed were attributed to normal animal variation. No treatment-related abnormalities were observed on necropsy. No treatment-related adverse findings were observed upon histologic evaluation of tissues.

Toxicokinetic parameters were estimated using WinNonlin pharmacokinetic software version 5.2.1 (Pharsight Corp.). A non-compartmental approach consistent with the extravascular route of administration was used for parameter estimation. All parameters were generated from individual amikacin and fosfomycin concentrations in plasma from Days 1 and 7. Plasma amikacin and fosfomycin concentration vs. time profiles were consistent with the inhalation dose route whereby a post-dose absorption phase was followed by a bi-phasic decline in plasma concentrations. Systemic exposure to both amikacin and fosfomycin was generally comparable between males and females and there was no clear indication of accumulation following repeat dosing. The peak plasma levels ($C_{max}$) for the high dose level on Day 7 ranged from 13.2 to 39.3 μg/mL for amikacin and 8.7 to 28.7 μg/mL for fosfomycin.

Based on the results of the study, significant exposure occurred following aerosol exposure to beagle dogs with no adverse effects observed over the 7 day treatment period. The NOAEL was considered to be 116.8 amikacin and 47.5 fosfomycin mg/kg/day delivered as a combination antibiotic aerosol. This is approximately 30 fold the estimated exposure to humans.

After completion of toxicity study in Example 3 above, a clinical study in a repeated dose, placebo controlled ascending format provided 6 dose levels of the 50 mg amikacin, 20 mg/mL fosfomcyin formulation in patients with VAT or VAP. The starting dose was 2 mL and the final dose was 12 mL. As each subject safely completed dose escalation, the next subject started at a higher initial dose. One dose level was given each day and three days were required to complete. Dose ascension occurred only if the patient did not have adverse effects such as significant bronchospasm (as measured by peak airway pressures) or oxygen desaturation, or any other moderate to severe adverse event. Serial tracheal aspirate and serum levels were collected for pK. Concomitant administration of IV antibiotics was allowed with the exception of amikacin in which case another IV aminoglycoside was substituted.

All references cited herein are specifically incorporated by reference.

What is claimed is:

1. A method to treat an acute pulmonary pathogenic bacterial infection during mechanical ventilation of a patient comprising:
    administering a combination of amikacin and fosfomycin at a ratio of amikacin to fosfomycin greater than 2.6:1.0 wherein the combination is dissolved in a hypertonic solution having at least about 30 equil/L of chloride ion and used to create an aerosol mist having a mean particle size less than 5 microns and an osmolality less than 1000 mOsmol/Liter; and
    wherein the aerosol mist is combined with humidified air during the mechanical ventilation and achieves a MIC90 against both a gram positive and a gram negative organism.

2. The method of claim 1, wherein the step of administering the combination uses an inline nebulizer operably connected to an airway of a mechanical ventilator.

3. The method of claim 1, wherein the osmolality of the aerosol mist is between 310 and 800 mOsmol/L.

4. The method of claim 1, wherein the administering step comprises delivering between about 100 and 300 mg fosfomycin within about 30 minutes.

5. The method of claim 4, wherein the administering step comprises delivering between about 150 and 600 mg amikacin within about 30 minutes.

6. The method of claim 2, wherein the humidified air is mixed with the aerosol mist in an airway of the mechanical ventilator.

7. The method of claim 1, wherein the administration step is triggered by inspiration.

8. The method of claim 6, wherein a positive pressure in the airway advances the humidified air through the in-line nebulizer to mix with the aerosol mist.

9. The method of claim 8, wherein the step of combining the humidified air with the aerosol mist increases a particle size of the aerosol mist by at least 10% and reduces the osmolality of the aerosol mist by at least 25%.

10. The method of claim 9, wherein the increased particle size is a mean greater than 3 microns and the reduced osmolality is less than 800 mOsmol/L.

11. The method of claim 1, wherein the gram positive organism is MRSA.

12. The method of claim 1, wherein the gram negative organism harbors a gene expressing a carbapenamase.

13. The method of claim 12, wherein the carbapenamase is NDM-1.

14. The method of claim 1, wherein the administering step comprises introducing the combination through the in-line nebulizer assembly connected proximal to a wye at the ventilator.

15. A method to treat ventilator associated pneumonia or ventilator associated tracheal bronchitis in a patient comprising:
    establishing assisted breathing for the patient through a positive pressure airway in a mechanical ventilator;
    introducing humidified air into the airway; and
    administering an aerosol combination of amikacin and fosfomycin at a ratio of amikacin to fosfomycin greater than 2.6:1.0, wherein the aerosol is created from a hypertonic solution having at least about 30 equil/L of permeant anion.

16. The method of claim 15, wherein the step of administering the aerosol combination is comprised of forming an aerosol mist of the hypertonic solution combined with the humidified air.

17. The method of claim 16, wherein the aerosol combination is formed by an in-line nebulizer operably connected to the ventilator airway.

18. The method of claim 17, wherein the in-line nebulizer has an inlet and an outlet in the ventilator airway such that positive pressure of air in the ventilator airway advances the aerosol mist from the nebulizer to the patient.

19. The method of claim 17, wherein the in-line nebulizer is operably connected to the airway proximal to a wye of the ventilator.

20. The method of claim 17, wherein the step of introducing humidified air into the airway is uninterrupted during operation of the in-line nebulizer.

21. The method of claim 20, wherein the humidified air is mixed with aerosol mist in the airway of the ventilator when triggered by inspiration by the patient.

22. The method of claim 21, wherein the mixture of the humidified air and the aerosol combination have an osmolality between about 310 and about 800 mOsmol/L.

23. The method of claim 21, wherein a mean particle size of the aerosol mist is less than 5 microns.

24. The method of claim 23, wherein the step of forming the aerosol mist in the in-line nebulizer is comprised of contacting the hypertonic solution with a vibrating membrane component of the nebulizer having a plurality of apertures therein with a diameter less than 2.5 microns.

25. The method of claim 15, wherein the administering step comprises delivery between about 100 and 300 mg fosfomycin within about 30 minutes.

26. The method of claim 25, wherein the administering step comprises delivery between about 150 mg and 600 mg amikacin within about 30 minutes.

27. A system comprising:
    a mechanical ventilator comprising an airway for transmitting positive air pressure generated by the ventilator to a patient,
    a source for humidified air operably connected to the airway, and an airway inlet fixture; and
    an in-line nebulizer operably connected to the airway at the airway inlet fixture, wherein the nebulizer comprises a reservoir containing a combination of amikacin and fosfomycin at a ratio of amikacin to fosfomycin greater than 2.6:1.0 in a hypertonic saline solution having at least about 30 equil/L permeant anion, and a vibrating plate membrane having a plurality of apertures with a diameter less than 2.5 microns.

28. The system of claim 27, wherein the nebulizer has an inlet and outlet each operably connected and sealed at the airway inlet fixture such that the nebulizer does not introduce additional air into the airway.

29. The system of claim 28, wherein the airway inlet fixture is disposed proximal to the ventilator wye piece.

30. The system of claim 29, wherein the in-line nebulizer has an annular vent space surrounding the vibrating membrane.

31. The system of claim 29, wherein the in-line nebulizer operates in a continuous mode to generate an aerosol mist.

32. The system of claim 27, further comprising an aerosol mist of the hypertonic solution having a mean particle size less than 5 microns and an osmolality less than 800 mOsmol/L.

33. The system of claim 27, wherein the reservoir contains between about 100 and about 300 mg fosfomycin and between about 150 and 650 mg amikacin.

34. The system of claim 27, further comprising a mixture of humidified air and the aerosol mist within the airway and distal to the in-line nebulizer.

35. The system of claim 34, further comprising an electric control unit to trigger administration of the mixture upon inspiration by the patient.

\* \* \* \* \*

UNITED STATES PATENT AND TRADEMARK OFFICE
CERTIFICATE OF CORRECTION

| | | |
|---|---|---|
| PATENT NO. | : 8,603,439 B2 | Page 1 of 1 |
| APPLICATION NO. | : 13/548115 | |
| DATED | : December 10, 2013 | |
| INVENTOR(S) | : Alan Bruce Montgomery | |

It is certified that error appears in the above-identified patent and that said Letters Patent is hereby corrected as shown below:

In the Specification

Column 3, line 17, change "hydroscopic" to -- hygroscopic --.

Column 4, line 11, change "hydroscopic" to -- hygroscopic --.

Column 11, line 54, change "hydroscopic" to -- hygroscopic --.

Column 12, line 4, change "hydroscopic" to -- hygroscopic --.

Column 12, lines 16-17, change "hydroscopic" to -- hygroscopic --.

Signed and Sealed this
Eleventh Day of March, 2014

Michelle K. Lee
*Deputy Director of the United States Patent and Trademark Office*